United States Patent
Bostick et al.

(10) Patent No.: US 10,600,507 B2
(45) Date of Patent: Mar. 24, 2020

(54) COGNITIVE NOTIFICATION FOR MENTAL SUPPORT

(71) Applicant: INTERNATIONAL BUSINESS MACHINES CORPORATION, Armonk, NY (US)

(72) Inventors: James E. Bostick, Cedar Park, TX (US); John M. Ganci, Jr., Cary, NC (US); Martin G. Keen, Cary, NC (US); Sarbajit K. Rakshit, Kolkata (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 280 days.

(21) Appl. No.: 15/423,798

(22) Filed: Feb. 3, 2017

(65) Prior Publication Data
US 2018/0225417 A1    Aug. 9, 2018

(51) Int. Cl.
| | |
|---|---|
| *G06Q 50/22* | (2018.01) |
| *G16H 10/60* | (2018.01) |
| *G06Q 50/00* | (2012.01) |
| *A61B 5/16* | (2006.01) |
| *A61B 5/00* | (2006.01) |
| *G16H 40/20* | (2018.01) |
| *G16H 50/70* | (2018.01) |
| *G16H 30/40* | (2018.01) |

(Continued)

(52) U.S. Cl.
CPC .......... *G16H 10/60* (2018.01); *A61B 5/0077* (2013.01); *A61B 5/165* (2013.01); *G06Q 50/01* (2013.01); *G16H 30/40* (2018.01); *G16H 40/20* (2018.01); *G16H 40/67* (2018.01); *G16H 50/30* (2018.01); *G16H 50/70* (2018.01); *A61B 5/4803* (2013.01); *A61B 2505/07* (2013.01)

(58) Field of Classification Search
CPC ...... G16H 10/60; G16H 40/20; A61B 5/0077; A61B 5/4803; G06F 19/3418; G06Q 50/10; G06Q 50/01
USPC ......................................................... 705/2–4
See application file for complete search history.

(56) References Cited

U.S. PATENT DOCUMENTS

| | | | |
|---|---|---|---|
| 9,305,140 B2 | 4/2016 | Federoff et al. | |
| 2007/0185732 A1* | 8/2007 | Hicks ................... | G06F 19/324 705/2 |

(Continued)

OTHER PUBLICATIONS

Schulz, Richard, and Lynn M. Martire. "Family caregiving of persons with dementia: prevalence, health effects, and support strategies." The American journal of geriatric psychiatry 12.3 (2004): 240-249.*

(Continued)

*Primary Examiner* — Mark Holcomb
(74) *Attorney, Agent, or Firm* — Scott Dobson; Andrew D. Wright; Roberts Mlotkowski Safran Cole & Calderon P.C.

(57) ABSTRACT

Systems and methods are disclosed for detecting a change in a person's mental state using biometric data and correlated social media content, and notifying a caregiver based on the detected change. A method includes: monitoring, by a computer device, biometric data of a user; monitoring, by the computer device, social media content of the user; determining, by the computer device and based on the biometric data and the social media content, that the user has experienced a changed mental state; and notifying, by the computer device, a caregiver of the changed mental state.

15 Claims, 3 Drawing Sheets

(51) Int. Cl.
*G16H 50/30* (2018.01)
*G16H 40/67* (2018.01)

(56) References Cited

U.S. PATENT DOCUMENTS

| | | | |
|---|---|---|---|
| 2008/0215370 A1* | 9/2008 | Dent | G06F 21/6245 705/3 |
| 2011/0119079 A1* | 5/2011 | Schoenberg | G06F 19/328 705/2 |
| 2012/0124122 A1 | 5/2012 | El et al. | |
| 2012/0165618 A1* | 6/2012 | Algoo | A61B 5/744 600/300 |
| 2013/0035946 A1* | 2/2013 | Ratan | G06F 19/3418 705/2 |
| 2013/0241719 A1 | 9/2013 | Biswas et al. | |
| 2014/0019468 A1* | 1/2014 | Federoff | G06N 5/04 707/758 |
| 2014/0324749 A1 | 10/2014 | Peters et al. | |
| 2014/0377727 A1 | 12/2014 | Yom-Tov et al. | |
| 2015/0067061 A1 | 3/2015 | Poston | |
| 2015/0161538 A1* | 6/2015 | Matus | G06Q 10/0635 705/4 |
| 2015/0302539 A1 | 10/2015 | Mazar et al. | |
| 2016/0147970 A1 | 5/2016 | Rosen et al. | |
| 2016/0283855 A1* | 9/2016 | Cecchi | G06N 7/005 |
| 2016/0341961 A1* | 11/2016 | Mullins | G06F 1/163 |

OTHER PUBLICATIONS

Vivion, "Know ye genotype: How to predict future behavior from past social media use", https://www.tnooz.com/article/know-ye-genotype-how-to-predict-future-behavior-from-past-social-media-use/, Tnooz, Jul. 10, 2013, 3 pages.

* cited by examiner

FIG. 3

COGNITIVE NOTIFICATION FOR MENTAL SUPPORT

BACKGROUND

The present invention generally relates to detecting and addressing changes in a person's mental state and, more particularly, to a cognitive system and method for detecting a change in a person's mental state using biometrics data and correlated social media content, and notifying a caregiver based on the detected change.

It is common to provide support to a person when they are experiencing an unwanted mental state such as anger, sadness, depression, fear, etc. These mental states are often triggered by events that occur in the person's life (e.g., life events) such as: death of loved one, illness of loved one, loss of job, divorce, separation, car accident, birth of child, birthday, anniversary, etc. Sometimes, these mental states are addressed by the person alone. Other times, these mental states are addressed with the assistance of a caregiver (e.g., family member, friend, co-worker, doctor, counselor, etc.).

SUMMARY

In a first aspect of the invention, there is a method that includes: monitoring, by a computer device, biometric data of a user; monitoring, by the computer device, social media content of the user; determining, by the computer device and based on the biometric data and the social media content, that the user has experienced a changed mental state; and notifying, by the computer device, a caregiver of the changed mental state.

In another aspect of the invention, there is a computer program product that includes a computer readable storage medium having program instructions embodied therewith. The program instructions are executable by a computing device to cause the computing device to: receive biometric data of a user from a biometric device; categorize the biometric data based on an amount of deviation from a normal range for the user; monitor social media content of the user; perform contextual analysis of the social media content to determine a topic of the social media content; correlate the social media content to the biometric data; determine, based on the topic of the social media content and the biometric data, that the user has a changed mental state; identify the changed mental state; select a caregiver based on the changed mental state; and send a notification to a computer device of the caregiver, the notification identifying the user and the changed mental state.

In another aspect of the invention, there is a system that includes: a CPU, a computer readable memory, and a computer readable storage medium associated with a computer device; program instructions to receive biometric data of a user from a biometric device; program instructions to categorize the biometric data based on an amount of deviation from a normal range for the user; program instructions to monitor social media content of the user; program instructions to perform contextual analysis of the social media content to determine a topic of the social media content; program instructions to determine, based on the topic of the social media content and the biometric data, that the user has a changed mental state; program instructions to select a caregiver from a plurality of pre-defined caregivers based on the changed mental state; and program instructions to send a notification to a computer device of the caregiver, the notification identifying the changed mental state. The program instructions are stored on the computer readable storage medium for execution by the CPU via the computer readable memory.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

The present invention generally relates to detecting and addressing changes in a person's mental state and, more particularly, to a cognitive system and method for detecting a change in a person's mental state using biometrics data and correlated social media content, and notifying a caregiver based on the detected change. Although topics of discussion often have an impact on a person's mental state, a caregiver typically does not have access to such discussions when providing support to the person experiencing the mental state. This lack of knowledge can hinder the ability of the caregiver to provide adequate support to the person experiencing the mental state. Aspects of the invention address this shortcoming by providing a cognitive method to perform real-time monitoring of a person's mental state learned from wearable biometrics data and correlated social media content or discussion types that are identified to impact the person's mental state. Based upon detecting a change in a person's mental state, a caregiver is identified and provided with the information (e.g., social media content) that is impacting the person's mental state in order to facilitate the caregiver providing mental support for the person.

In embodiments, a change in the person's mental state is detected based on biometrics data and correlated social media content. At least one of tonal analysis and facial expression analysis may additionally be used in determining the person's changed mental state. Cognitive methods are used to determine a topic of the social media content associated with the change in the mental state. An appropriate caregiver is identified based on the detected mental state and the determined topic, and the person and the identified caregiver are notified of the detected mental state and the determined topic. The identified caregiver may be provided with unrestricted information, such as publicly posted social media content, that is affecting the person's mental state. With consent of the person, the identified caregiver may also be provided with restricted information, such as private social media content, that is affecting the person's mental state. Implementations of the invention thus facilitate the caregiver providing mental support for the person by providing the caregiver with an indication of the detected mental state and the information (e.g., social media content) that is correlated with the detected mental state.

Aspects of the invention are additionally directed to optimizing the identification of the appropriate caregiver based on: a biometrics feedback loop for given topic; and evaluation of effectiveness in a hierarchy of defined or learned caregivers, with data positively impacting the person's mood from providing mental support. Plural caregivers may be defined for a single person and the effectiveness of each caregiver may be monitored with respect to detected mental states and correlated topics. In embodiments, the system is configured to learn, based on historical effectiveness, a hierarchy of the plural caregivers for a particular mental state and correlated topic for a person. For example, the system may learn from past results that family member "A" is the best caregiver for a particular mental state and correlated topic for this person, family member "B" is the second best caregiver for the same mental state and correlated topic for this person, and family member "C" is the third best caregiver for the same mental state and correlated topic for this person. In this manner, when the system detects the particular mental state and correlated topic for this person, the system first attempts to notify family member "A" to step in as a caregiver. In the event that family member "A" is not available, then the system attempts to notify family member "B". In the event that family member "B" is not available, then the system attempts to notify family member "C".

Additional aspects of the invention are directed to monitoring the effectiveness of caregivers and providing for an escalation of caregivers. In embodiments, the system monitors the effectiveness of a caregiver in real-time while the caregiver is providing support to the person with the detected mental state. The system may configured to determine, based on the monitored effectiveness, that the caregiver is not effectively helping the person, in which case the system notifies another caregiver such as a counselor or medical doctor as part of an escalation.

Further aspects of the invention are directed to an effectiveness measure of the caregiver. In embodiments, an effectiveness of a caregiver is measured in ranges of biometrics feedback such as defined ranges for normal pulse of user (e.g., pulse in a range of 60-70), upset (e.g., pulse in a range of 71-80), and very agitated (e.g., pulse in a range of 81-100). Alternatively, the effectiveness can be measured from a change in biometrics feedback before the correlated social feedback, and drop in biometrics if effective prior to the incident.

Aspects of the invention are also directed to a visualization of real-time feedback. In embodiments, the caregiver providing mental support to the person can measure the effectiveness of the support through real-time visualization of biometrics feedback as they are communicating with the person receiving the support. For example, the person's real-time biometric data may be displayed to the caregiver via a mobile app, thus providing the caregiver real-time feedback of whether the support is effective in changing the person's mental state.

Implementations of the invention described herein may be used to provide a computer-implemented method that includes: capturing user mental condition data from at least one mental condition data source; and determining a user mental state from the user mental condition data. The mental condition data source may include at least one of: social media content of the user; biometric data of the user; audio interaction data obtained from recording the user interacting with at least one person; and visual interaction data obtained from observing the user interacting with at least one person. The determining step may include determining a change in a mental condition of the user based on change in the mental condition data. The method may include determining, based on the change in mental condition data, if a topic exposed to a user causes the change in mental condition.

In the computer-implemented method, the mental condition data source includes at least one of (i) the audio interaction data obtained from recording the user communicating with at least one person, and (ii) the visual interaction data obtained from observing the user interacting with at least one person, wherein both the audio interaction data and the visual interaction relate to an interaction involving a family member of the user. The method may also include determining a bond strength between the family member of the user and the user based on the mental condition data. The method may additionally include: determining if the change in mental condition exceeds a certain threshold; and determining whether or not the user requires mental health treatment based on the threshold determination, wherein the threshold is based on the topic exposed to the user. The method may further include: determining, based on the mental condition data, if the at least one family member meets a friendship threshold with the user; determining whether to share restricted or unrestricted mental condition data with the at least one family member based on the friendship threshold determination step; and determining whether the at least one family member can offer support to the user based on the identified topic and the mental health data.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
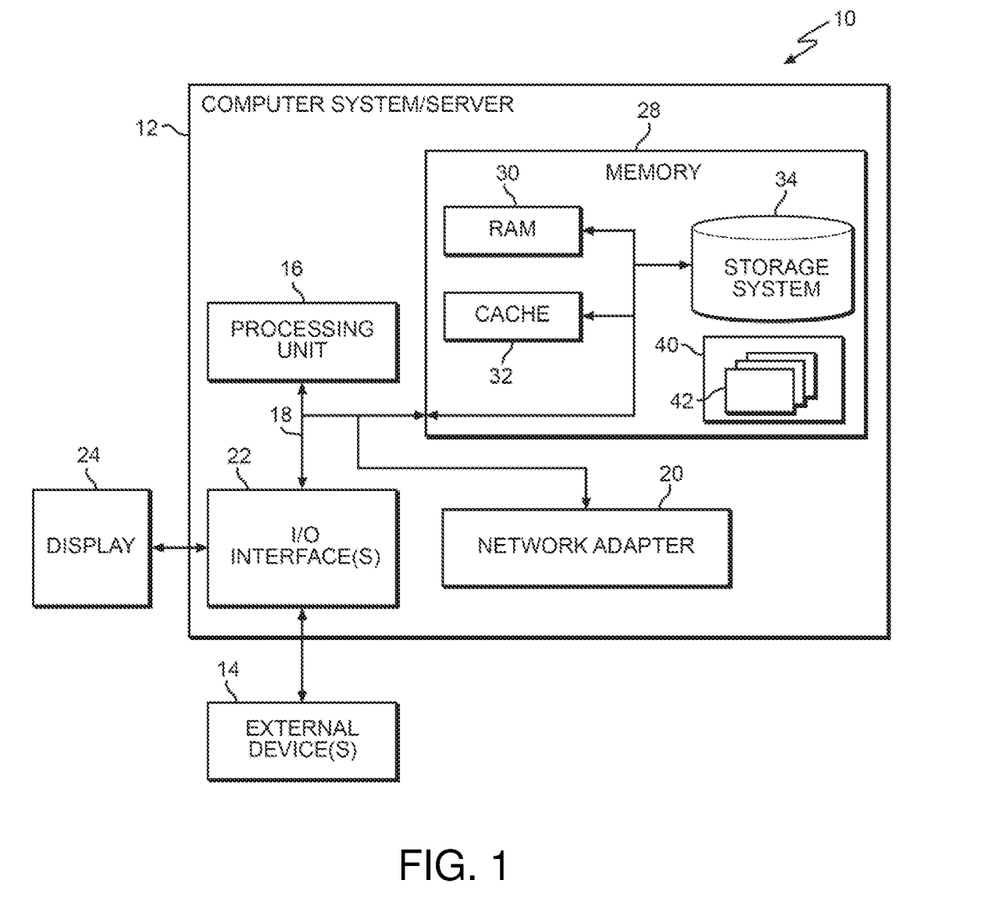
FIG. 1 depicts a computing infrastructure according to an embodiment of the present invention.

Referring now to FIG. 1, a schematic of an example of a computing infrastructure is shown. Computing infrastructure 10 is only one example of a suitable computing infrastructure and is not intended to suggest any limitation as to the scope of use or functionality of embodiments of the invention described herein. Regardless, computing infrastructure 10 is capable of being implemented and/or performing any of the functionality set forth hereinabove.

In computing infrastructure 10 there is a computer system (or server) 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system executable instructions, such as program modules, being executed by a computer system. Generally, program modules may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system 12 in computing infrastructure 10 is shown in the form of a general-purpose computing device. The components of computer system 12 may include, but are not limited to, one or more processors or processing units (e.g., CPU) 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc.

Figure 2:
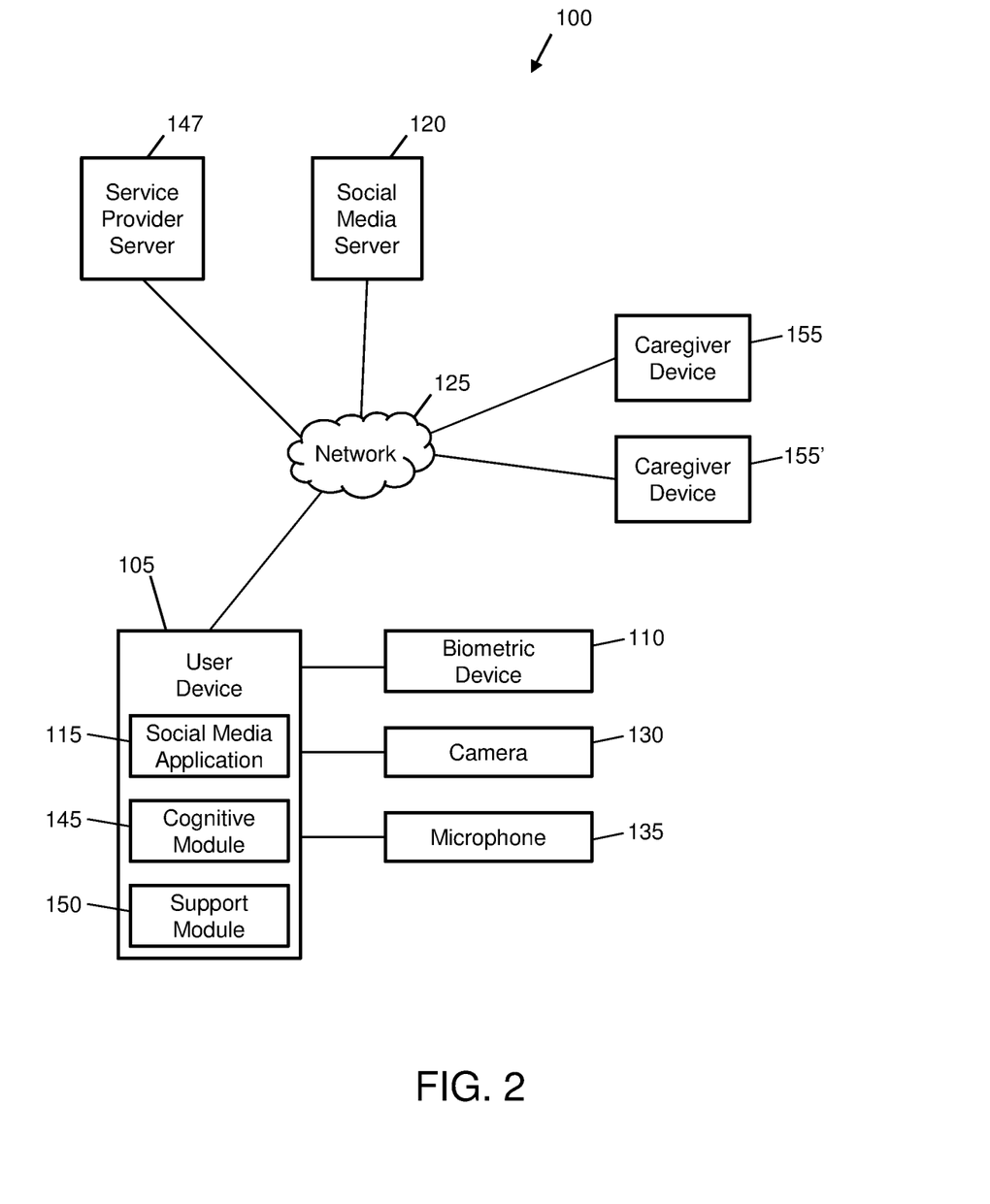
FIG. 2 shows a block diagram of an exemplary system in accordance with aspects of the invention.

FIG. 2 shows a block diagram of an exemplary system 100 in accordance with aspects of the invention. In embodiments, the system 100 includes a user device 105 that receives biometric data of a user from a biometric device 110. The user device 105 is a computer device such as a smartphone, tablet computer, laptop computer, desktop computer, etc., and may include one or more elements of the computer system 12 of FIG. 1. The biometric device 110 is a sensor device that detects at least one type of biometric data of a user. The biometric device 100 may comprise, for example, a smart watch, wrist band, chest band, earpiece, etc., that is worn by a user, and may be configured to detect a pulse or heart rate of the user. Other types of biometric devices may be used and other types of biometric data may be collected. The biometric device 110 is configured to communicate with the user device 105 to transfer the user's detected biometric data to the user device 105. The communication between the biometric device 110 and the user device 105 may be wireless (e.g., via Bluetooth pairing) or wired.

The biometric device 110 may alternatively comprise a smart contact lens (referred to as a smart contact) worn on the eye of the user. For example, a smart contact may have an inward facing camera that is used to observe the pupil dilation as a method of measuring an emotional state of the user. The smart contact may be configured to stream the biometric data to the user device 105 (e.g., by Bluetooth) or directly to a cloud service via WiFi.

In embodiments, the user device 105 includes at least one social media application 115 that is configured to provide the user the ability to send and receive social media content via the user device 105. The social media application 115 may comprise a software program, such as a program module 42 of FIG. 1, that is stored in a memory of the user device 105 and run by a processor of the user device 105. The social media application 115 may communicate with a social media server 120 via a network 125. For example, the user may input credentials via the social media application 115 to log in to their account with the social media server 120, after which the user may use the social media application 115 to post content in their social media account and to view and comment on content in other users' social media accounts, e.g., in a conventional manner. Aspects of the invention are described herein using an example of a single social media application 115, but it is understood that the user device 105 may include plural different social media applications 115 associated with plural different social media servers 120. The content that the user inputs via the one or more social media applications 115 is collectively referred to as social media content, and may include, but is not limited to: text (e.g., posts, comments, discussions, etc.); photos; likes/dislikes; plus/minus one; status; and emoji. The social media content may include content that is posted by the user as well as content of other users that is viewed by the user.

The network 125 may include a general wide area network (WAN) and/or a public network (e.g., the Internet). The network 125 may be part of a cloud environment.

In embodiments, the user device 105 receives image data from a camera 130. The camera 130 may be integrated with the user device 105 (e.g., such as a camera that is integrated with a smartphone). Alternatively, the camera 130 may be separate from the user device 105 and communicate with the user device 105 via wired or wireless communication. The camera 130 is configured to capture image data of the user's facial expressions.

In embodiments, the user device 105 receives audio data from a microphone 135. For example, the user device 105 may include the microphone 135 and a speaker that permit the user device 105 to function as a telephone or video call device. The microphone 135 receives audio data, e.g., spoken words, from a user of the user device 105. In additional aspects, the user device 105 may receive audio data from passive listening devices. For example, one or more other mobile devices and/or wearable devices may be configured to capture audio data of the user and stream the audio data to the user device 105, which may analyze the audio data using tone analysis as described herein.

According to aspects of the invention, the user device 105 includes a cognitive module 145 that is configured to cognitively analyze data from at least one of the social media applications 115, the camera 130, and the microphone 135. The cognitive module 145 may comprise a software program, such as at least one program module 42 of FIG. 1, that is stored in a memory of the user device 105 and run by a processor of the user device 105. In embodiments, the cognitive module 145 is configured to perform contextual analysis of the user's social media content (from the social media applications 115) to determine a topic and/or sentiment of the social media content. The cognitive module 145 may also be configured to perform facial pattern analysis of the image data from the camera 130, where the facial pattern analysis may be used in determining a mood of the user. For example, the cognitive module 145 may include a facial pattern analyzer module that determines an emotion such as anger, fear, anticipation, surprise, joy, sadness, trust, and disgust, from the images of the user's face. The cognitive module 145 may also be configured to perform tone analysis of the audio data from the microphone 135, where the tone analysis may be used in determining a mood of the user. For example, the cognitive module 145 may include a tone analyzer module that determines an emotion such as anger, fear, anticipation, surprise, joy, sadness, trust, and disgust, from the tone of the user's spoken words.

Alternatively to residing on the user device 105, some or all the components of the cognitive module 145 may be located at the social media server 120 and/or a third party server 147. In this manner, the computing resources and processes associated with the cognitive module may be provided as a service (e.g., a cloud service) to the user device 105.

In accordance with aspects of the invention, the user device 105 includes a support module 150 that is configured to determine a mental state of the user based on the biometric data (from the biometric device 110) and the social media content (from the social media application 115). In embodiments, the support module 150 correlates the social media content to the biometric data and determines when: (i) the user's biometric data deviates from a normal range for this user; and (ii) a topic or sentiment of the user's social media content matches a predefined or learned topic or sentiment. When both conditions (i) and (ii) are satisfied concurrently, the support module 150 determines that the user's mental state has changed. As used herein, concurrently refers to the two conditions occurring within a predefined time of one another. The predefined time may be any appropriate value, such as three minutes, and may be defined by the user via a user interface of the support module 150.

In embodiments, the support module 150 determines when the user's biometric data deviates from a normal range for this user by comparing the currently detected biometric data to a stored normal range for this user. For example, the support module 150 may store data defining a normal range of heart rate for this user. The data defining the normal range may be predefined (e.g., input to the user device 150 by the user) or may be learned (e.g., by the support module 150 determining an average heart rate from historical biometric data from the biometric device 110). The amount of deviation may be categorized, e.g., into tiers, which information may be used in identifying a caregiver. In a non-limiting example, a user's normal range of heart rate may be 60-80 beats per minute (bpm). A detected heart rate (i.e., detected by the biometric device 110) that exceeds the normal range by 1-10 bpm may be deemed a first tier deviation. A detected heart rate that exceeds the normal range by 11-20 bpm may be deemed a second tier deviation. A detected heart rate that exceeds the normal range by 21-30 bpm may be deemed a third tier deviation. A detected heart rate that exceeds the normal range by 31 or more bpm may be deemed a fourth tier deviation.

In embodiments, the support module 150 determines when a topic or sentiment of the user's social media content matches a predefined or learned topic or sentiment by comparing the determined topic or sentiment to at least one stored topic or sentiment. For example, the support module 150 may store data defining a list of topics or sentiments that are deemed to trigger a change in mental state for this user. The data defining the list of topics or sentiments may be predefined via input to the user device 150 by the user. Predefined topics may include but are not limited to: divorce, separation, death, job loss. Predefined sentiments may include but are not limited to: anger, fear, sadness. Additionally or alternatively, the data defining the list of topics or sentiments may be learned by the support module 150 based on historic data for this user.

In accordance with aspects of the invention, based upon determining that the user's mental state has changed, the support module 150 identifies the changed mental state of the user. In embodiments, the support module 150 identifies the changed mental state based on at least one of: contextual analysis of the social media content; facial pattern analysis of the image data from the camera 130; and tone analysis of the audio data from the microphone 135. The support module 150 may be programmed to categorize the results of these analyses into predefined mental states, such as anger, fear, anticipation, surprise, joy, sadness, trust, and disgust. Aspects of the invention are not limited to these exemplary mental states, however, and different mental states may be used.

According to aspects of the invention, based upon determining that the user's mental state has changed and identifying the changed mental state, the support module 150 determines whether the user's changed mental state necessitates support of a caregiver. In embodiments, the support module 150 is configured to filter out some changed mental states as not rising to the level of requiring support from the caregiver. For example, a user experiencing one of anticipation, surprise, joy, and trust rarely requires support of a caregiver. As such, when the changed mental state is one of these emotions, the support module 150 determines that a caregiver need not be notified.

In another example, the amount of biometric data deviation from normal (for this user) is used in determining whether to contact a caregiver. For example, a user experiencing a low level biometric change (e.g., a first tier deviation) likely does not require support of a caregiver. On the other hand, a user experiencing a higher level of biometric change (e.g., a second, third, or fourth tier deviation) might benefit from receiving support of a caregiver.

In another example, the determined topic of the social media content is used in determining whether to contact a caregiver. For example, a user experiencing a biometric change in association with one of the predefined or learned topics (e.g., divorce, separation, death, job loss) might benefit from receiving support of a caregiver. On the other hand, a user experiencing a biometric change in association with a topic that it not of concern to this user (e.g., a topic that is not included in the list of predefined or learned topics) likely does not require support of a caregiver.

Accordingly, in embodiments, the support module 150 is configured to determine whether support of a caregiver is needed based on at least one of: the changed mental state;

the amount of biometric data deviation from normal for this user; and the determined topic of the social media content. In an exemplary implementation, the support module 150 is configured to determine that support of a caregiver is necessary when the following conditions are met: (i) the changed mental state is one of a subset of the possible mental states (e.g., is one of anger, fear, sadness, and disgust); (ii) the amount of biometric data deviation from normal exceeds a predefined level (e.g., i.e., is one of a second, third, or fourth tier deviation); and (iii) the determined topic of the social media content is one of the predefined or learned topics (e.g., divorce, separation, death, job loss). Implementations of the invention are not limited to this example, and instead the support module 150 can be programmed to make this determination using other appropriate combinations and thresholds of these and/or other parameters.

In accordance with aspects of the invention, based on determining that support of a caregiver is needed, the support module 150 identifies (e.g., selects) a caregiver for the user that is experiencing the changed mental state. In embodiments, the support module 150 stores data defining at least one caregiver for each user. Typically, plural different caregivers are defined for each user. A caregiver can be any trusted person whose identification as a caregiver is input by the user. For example, a caregiver may be any of family member, friend, co-worker, neighbor, doctor, counselor, etc.

In embodiments, the support module 150 selects a caregiver based on comparing the user-defined caregivers and associations to at least one of the changed mental state, the amount of biometric data deviation from normal, and the determined topic of the social media content. In embodiments, the support module 150 provides the user with a user interface (UI) by which the user can input data defining the at least one caregiver. For each defined caregiver, the user may input data such as, but not limited to: name; contact information (e.g., telephone number, email address, etc.); relationship to user; and whether the caregiver is granted access to restricted information. Also via the UI, the user may provide input to define associations of respective caregivers with respective mental states and/or topics. For example, the user may wish to define that caregiver "A" is the desired caregiver when the changed mental state is fear, and that caregiver "B" is the desired caregiver when the topic is death in the family. The UI may be configured to permit the user to define a desired (e.g., primary) caregiver and an alternate (e.g., secondary) caregiver for each changed mental state. The UI may be configured to permit the user to define a desired (e.g., primary) caregiver and an alternate (e.g., secondary) caregiver for each predefined topic or sentiment. The UI may be configured to permit the user to define a desired (e.g., primary) caregiver and an alternate (e.g., secondary) caregiver for each tier of biometric data deviation.

In embodiments, the selection of the caregiver may also be based on effectiveness scores of different caregivers for this user. As described herein, each caregiver may be associated with one or more effectiveness scores, and the selection of the caregiver may be based on these measures of effectiveness. For example, a user may initially indicate that caregiver "A" is preferred for a particular changed mental state and topic. Over time the system may learn, through effectiveness measures and scores, that caretaker "B" is more effective at supporting the user for the particular changed mental state and topic. Based on this learned effectiveness, and with consent of the user, the system would select caretaker "B" over caretaker "A" for subsequent instances of providing support for the user for the particular changed mental state and topic.

According to aspects of the invention, the support module 150 notifies the identified caregiver using the contact information stored in association with the identified caregiver. For example, the support module 150 may send a notification comprising at least one of an SMS message and/or an email to a computer device 155 of the caregiver. In embodiments, the notification includes: the user's name or other identifying information; an indication of the changed mental state (e.g., anger, fear, sadness, disgust); an indication of the topic of the social media content that is correlated to the changed mental state (e.g., divorce, separation, death, job loss); and an indication of the amount of biometric data deviation from normal exceeds a predefined level (e.g., the user's heart rate is "x" bpm above normal). In some embodiments, the notification may include unrestricted information, such as the user's publicly posted social media content, that is correlated with the changed mental state. In some embodiments, and with consent of the user, the notification may include restricted information, such as the user's private social media content, that is correlated with the changed mental state. In this manner, the caregiver is provided with information that is correlated with the changed mental state, with the goal of permitting the caregiver to leverage the information to tailor their support that is provided to the user.

In embodiments, the support module 150 also notifies the user of the changed mental state. In some situations, a person can cope with a changed mental state on their own if they are alerted to the changed mental state. Accordingly, in embodiments, the support module 150 is configured to display a notification on the user device 105 that indicates the changed mental state. The notification can also include at least one of: an indication of the topic of the social media content (e.g., divorce, separation, death, job loss); and an indication of the amount of biometric data deviation from normal exceeds a predefined level (e.g., your heart rate is "x" bpm above normal); and an indication of the caregiver that has been notified.

According to aspects of the invention, the notified caregiver is provided with real-time biometrics data of the user from the biometric device 110. In embodiments, the biometric data is communicated from the biometric device 110 to the user device 105, and from the user device 105 to the caregiver device 155 where it is visually displayed while the caregiver is providing support to the user. In this manner, the caregiver can see in real-time if the user's biometric data returns to the normal range. This helps the caregiver measure the effectiveness of the support that they are providing to the user.

In accordance with additional aspects of the invention, the effectiveness of the caregiver that is providing support to the user may be determined. The effectiveness of the caregiver may be determined based on at least one of: input from the caregiver; input from the user; and automatic measurement of reduction of the biometric data deviation during the support provided by the caregiver. For example, when a caregiver provides support, software of the system may be configured to evaluate the emotional state feedback methods available to determine the effectiveness of the caregiver for a given topic.

In embodiments, the support module 150 optimizes selecting (i.e., identifying) a caregiver based on historical results of effectives for respective caregivers. Each caregiver defined by a user may be associated with a respective effectiveness score that is automatically adjusted by the support module 150 based on the determined effectiveness of a caregiver. In this manner, a caregiver's effectiveness score may be increased when it is determined that the caregiver has provided effective support to the user, and the caregiver's effectiveness score may be decreased when it is determined that the caregiver has provided ineffective support to the user. Each caregiver may have a general effectiveness score that is independent of mental state or topic. Additionally or alternatively, each caregiver may have plural different effectiveness scores for different mental states and/or topics for a single user. In this manner, a single caregiver may have a relatively high effectiveness score for a user for a first topic, and a relatively low effectiveness score for the same user for a second topic different from the first topic. In this manner, the support module 150 is configured to learn, based on historical measures of effectiveness, an optimal caregiver for a particular mental state and/or topic for a user.

In embodiments, the support module 150 is configured to escalate caregiver notification based on a determined effectiveness of the support provided by a caregiver. For example, the support module 150 may determine in realtime, based on the user's biometric data, that the support being provided by a caregiver is not effective. In this situation, the support module 150 may be configured to notify a second caregiver of the user's changed mental state. The second caregiver may be, for example, a user-defined medical professional. In this embodiment, the support module 150 sends a notification to a computer device 155' of the second caregiver, which notification may include the same information that was included in the notification that was previously sent to the computer device 150 of the initial caregiver.

Figure 3:
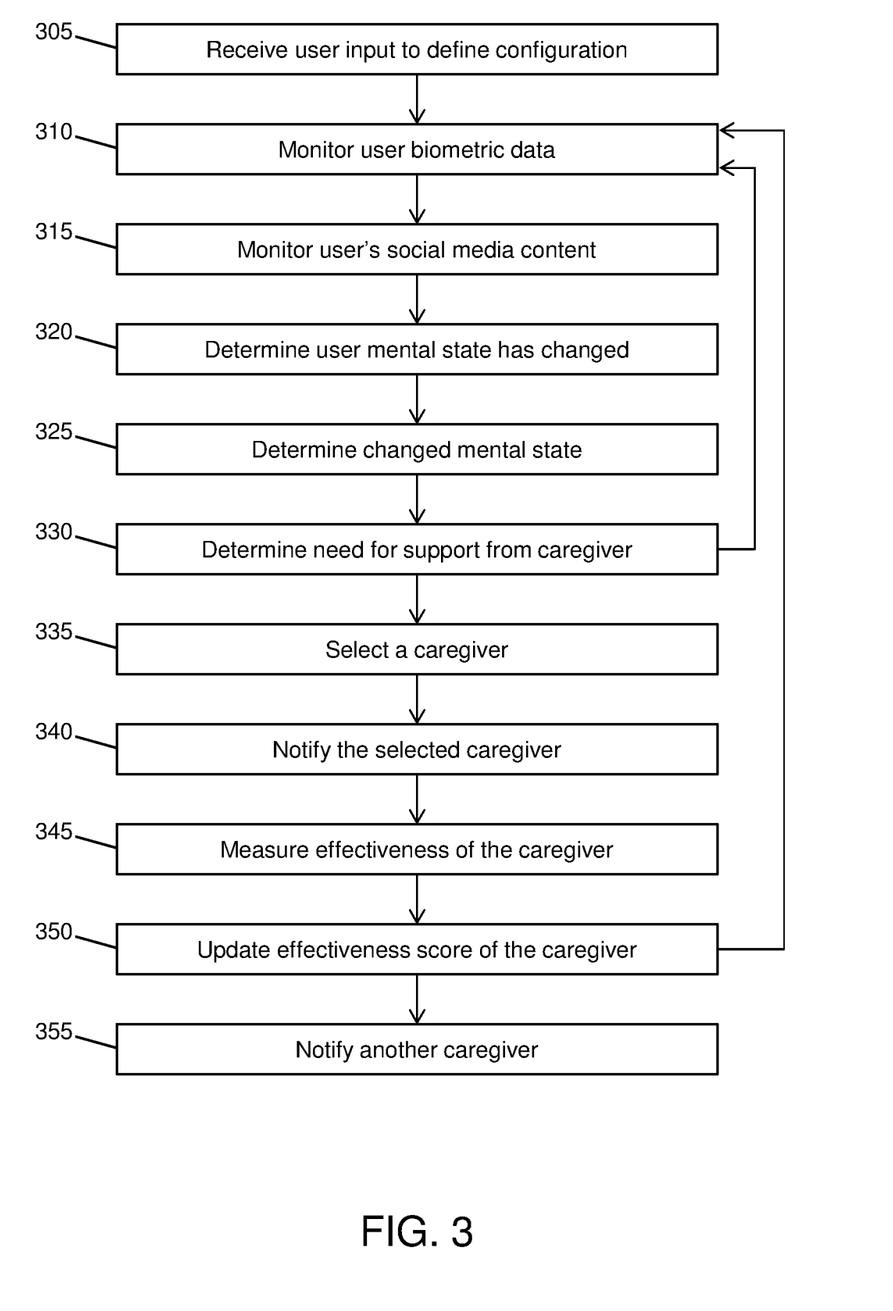
FIG. 3 shows a flowchart of a method in accordance with aspects of the invention.

FIG. 3 shows a flowchart of a method in accordance with aspects of the invention. The steps of the method may be performed in the system of FIG. 2 and are described with reference to the elements and steps described with respect to FIG. 2.

At step 305, a system receives user input that defines a configuration for the user. In embodiments, the support module 150 generates a user interface (UI) that is displayed on a user device 105, and the user provides input via the UI. The input may comprise information including but not limited to: the user's normal range of biometric data; the user's social media account(s) to monitor; predefined topics; predefined sentiments; and caregiver information such as caregiver name, caregiver contact information, caregiver relationship to user, and whether the caregiver is granted access to restricted information. The input at step 305 may be received directly at the user device 105, or may be received at a different computer device and communicated to the user device 105.

At step 310, the system monitors the user's biometric data. In embodiments, and as described with respect to FIG. 2, a biometric device 110 may be used to detect at least one parameter of biometric data of the user, such as heart rate. The biometric device 110 may communicate the biometric data to the user device 105. As described with respect to FIG. 2, the user device 105 may categorize the biometric data into predefined tiers. The biometric data may be time-stamped for correlating to other data.

At step 315, the system monitors the user's social media content. In embodiments, and as described with respect to FIG. 2, the user device 105 may monitor the content that the user posts and/or views via at least one social media application 115. The social media content may be time-stamped for correlating with the time-stamp of the biometric data of this same user. In embodiments, step 315 may include a cognitive module 145 performing contextual analysis of the user's social media content to determine a topic and/or sentiment of the social media content, as described herein. Step 315 may include obtaining image data from a camera 130 while the user is posting and/or viewing the social media content. Step 315 may include obtaining audio data from a camera microphone 135 while the user is posting and/or viewing the social media content.

At step 320, the system determines whether the user's mental state has changed. Step 320 may be performed in the manner described with respect to FIG. 2. In embodiments, the support module 150 determines whether the user's mental state has changed based on a combination of the biometric data and the social media content. For example, the support module 150 correlates the user's social media data to the user's biometric data to determine when (i) the user's biometric data deviates from a normal range and (ii) a topic or sentiment of the user's social media data matches a predefined topic or sentiment. When both conditions (i) and (ii) are satisfied concurrently, the support module 150 determines that the user's mental state has changed.

At step 325, the system identifies the changed mental state. In embodiments, and as described with respect to FIG. 2, the support module 150 identifies the changed mental state based on at least one of: contextual analysis of the social media content; facial pattern analysis of the image data from the camera 130; and tone analysis of the audio data from the microphone 135.

At step 330, the system determines whether the changed mental state necessitates support from a caregiver. As described with respect to FIG. 2, the support module 150 may be configured to determine whether support of a caregiver is needed based on at least one of: the changed mental state; the amount of biometric data deviation from normal for this user; and the determined topic of the social media content. The support module 150 may filter out (e.g., exclude) certain changed mental states (e.g., anticipation, surprise, joy, etc.) as not necessitating support from a caregiver. The support module 150 may filter out (e.g., exclude) certain biometric data deviations (e.g., lowest level deviations) as not necessitating support from a caregiver.

In the event that the changed mental state does not require support from a caregiver, then the process returns to step 310. In the event that the changed mental state does require support from a caregiver, then the process proceeds to step 335.

At step 335, based on determining that the changed mental state does require support from a caregiver, the system selects a caregiver. Step 335 may be performed in the manner described with respect to FIG. 2. For example, the support module 150 may select the caregiver based on at least one of: user-defined associations; the changed mental state; the amount of biometric data deviation from normal; the determined topic of the social media content; and effectiveness of the caregiver.

At step 340, the system notifies the selected caregiver. In embodiments, and as described with respect to FIG. 2, the user device 105 may send a notification to a computer device 150 of the selected caregiver. The notification may include, for example: the user's name or other identifying information; an indication of the changed mental state (e.g., anger, fear, sadness, disgust); an indication of the topic of the social media content that is correlated to the changed mental state (e.g., divorce, separation, death, job loss); and an indication of the amount of biometric data deviation from normal exceeds a predefined level (e.g., the user's heart rate is "x"

bpm above normal). In some embodiments, the notification may include unrestricted information, such as the user's publicly posted social media content, that is correlated with the changed mental state. In some embodiments, and with consent of the user, the notification may include restricted information, such as the user's private social media content, that is correlated with the changed mental state.

Step 340 may also include providing real-time biometric data to the selected caregiver. As described with respect to FIG. 2, the user device 105 may be configured to send real-time biometric data received from the biometric device 110 to the caregiver device 150 for display on the caregiver device 150.

Step 340 may also include notifying the user that the caregiver has been notified. For example, the user device 105 may display a notification that indicates the changed mental state. The notification can also include at least one of: an indication of the topic of the social media content (e.g., divorce, separation, death, job loss); and an indication of the amount of biometric data deviation from normal exceeds a predefined level (e.g., your heart rate is "x" bpm above normal); and an indication of the caregiver that has been notified.

At step 345, the system measures an effectiveness of the caregiver that provides support to the user. Step 345 may be performed in the manner described with respect to FIG. 2, e.g., by using at least one of: feedback input by the user; feedback input by the caregiver; and automated measures of effectiveness.

At step 350, the system updates an effectiveness score of the caregiver based on the measured effectiveness from step 345. In embodiments, the system stores data defining one or more effectiveness scores for each caregiver, and step 350 includes updating the appropriate effectiveness score based on the results for this instance of providing support. In this manner, the system may learn the effectiveness of different caregivers for different users and different situations, thus optimizing the selection of a caregiver in a future situation.

At step 355, the system notifies a second caregiver. In embodiments, and as described with respect to FIG. 2, the system may determine in real time that the support being provided by the caregiver (selected at step 335) is not effective. In this situation, the support module 150 sends a notification to a computer device 155' of the second caregiver, which notification may include the same information that was included in the notification that was previously sent to the computer device 150 of the initial caregiver.

In embodiments, a service provider, such as a Solution Integrator, could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still additional embodiments, the invention provides a computer-implemented method, via a network. In this case, a computer infrastructure, such as computer system 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. A computer implemented method, comprising:
A computer implemented method, comprising:
monitoring, by a computer device, biometric data of a user;
monitoring, by the computer device, social media content of the user; and
determining, by the computer device and based on the biometric data and the social media content, that the user has experienced a changed mental state;
wherein the determining that the user has a changed mental state is based on the monitoring of the biometric data by monitoring the user's heart rate using a heart rate sensor, and by monitoring the social media content by performing a contextual analysis of the social media content to determine a topic of the social media content and a sentiment of the user while engaging in communicating on social media regarding the topic of the social media content,
wherein the sentiment of the user is determined by using at least one selected from a group consisting of: facial analysis using a camera; and tonal analysis using a microphone, and
wherein the determining that the user has experienced a changed mental state comprises:
correlating the social media content and the biometric data; and
determining that the biometric data deviates from a normal range of the heart rate concurrently with the determined topic of the social media content matching a predefined topic and the determined sentiment matching a predefined sentiment,
further comprising:
selecting a caregiver from among a plurality of caregivers based on a biometric feedback loop analysis using the biometric data for the determined topic and an evaluation of past effectiveness of each of the caregivers in providing a positive impact on the user's sentiments in the past with regard to the determined topic, wherein the positive impact is determined by improvements in the user's biometric data and in determined sentiments of the user for the determined topic of the social media content; and
notifying, by the computer device, the selected caregiver of the changed mental state.
2. The method of claim 1, wherein the monitoring the biometric data comprises the computer device receiving the biometric data from a biometric device.

3. The method of claim 2, wherein the monitoring the biometric data comprises categorizing the biometric data according to an amount of deviation from a normal range of biometric data associated with the user.

4. The method of claim 1, wherein the selecting the caregiver is further based on user-defined associations regarding each of the plurality of caregivers.

5. The method of claim 1, wherein the notifying the selected caregiver comprises the computer device sending a notification message to a computer device of the caregiver.

6. The method of claim 5, wherein the notification message comprises at least one from the group consisting of: a user identifier; an indication of the changed mental state; an indication of a topic of the social media content that is correlated to the changed mental state; and an indication of an amount of deviation of the biometric data deviation from a normal range for this user; unrestricted user information; and restricted user information.

7. The method of claim 5, further comprising the computer device sending real-time biometric data to the computer device of the selected caregiver while the caregiver is providing support to the user.

8. The method of claim 5, further comprising the computer device displaying a message notifying the user that the caregiver has been notified.

9. The method of claim 1, further comprising measuring an effectiveness of the selected caregiver based on the caregiver providing support to the user.

10. The method of claim 9, further comprising updating an effectiveness score of the selected caregiver based on the measuring.

11. The method of claim 9, further comprising:
determining, by the computer device and based on the measuring, that additional support is needed; and
notifying, by the computer device, another caregiver of the changed mental state.

12. A computer program product comprising a computer readable storage medium having program instructions embodied therewith, the program instructions executable by a computer device to cause the computer device to:
receive biometric data of a user from a biometric device;
categorize the biometric data based on an amount of deviation from a normal range for the user;
monitor social media content of the user;
perform contextual analysis of the social media content to determine a topic of the social media content;
determine, based on the topic of the social media content and the biometric data, that the user has a changed mental state; and
identify the changed mental state;
wherein the determining that the user has a changed mental state is based on the monitoring of the biometric data by monitoring the user's heart rate using a heart rate sensor, and by monitoring of the user's pupil dilation using a smart contact lens on an eye of the user having an inward facing camera to observe the pupil dilation of the user, and by performing the contextual analysis of the social media content to determine the topic of the social media content and a sentiment of the user while engaging in communicating on social media regarding the topic of the social media content,
wherein the sentiment of the user is determined by using at least one selected from a group consisting of: facial analysis using a camera; and tonal analysis using a microphone,
wherein the determining that the user has experienced a changed mental state further comprises:
correlating the social media content and the biometric data; and
determining that the biometric data deviates from a normal range of the heart rate concurrently with the determined topic of the social media content matching a predefined topic and the determined sentiment matching a predefined sentiment, and
wherein the program instructions are further executable by the computer device to cause the computer device to:
select a caregiver from among a plurality of caregivers based on a biometric feedback loop analysis using the biometric data for the determined topic and an evaluation of past effectiveness of each of the caregivers in providing a positive impact on the user's sentiments in the past with regard to the determined topic, wherein the positive impact is determined by improvements in the user's biometric data and in determined sentiments of the user for the determined topic of the social media content; and
notify the selected caregiver of the changed mental state.

13. The computer program product of claim 12, wherein the program instructions cause the computer device to:
measure an effectiveness of the caregiver based on the caregiver providing support to the user; and
update an effectiveness score of the caregiver based on the measuring.

14. A system, comprising:
a CPU, a computer readable memory, and a computer readable storage medium associated with a computer device;
program instructions to receive biometric data of a user from a biometric device;
program instructions to categorize the biometric data based on an amount of deviation from a normal range for the user;
program instructions to monitor social media content of the user;
program instructions to perform contextual analysis of the social media content to determine a topic of the social media content; and
program instructions to determine, based on the topic of the social media content and the biometric data, that the user has a changed mental state,
wherein the program instructions are stored on the computer readable storage medium for execution by the CPU via the computer readable memory, and
wherein the determining that the user has a changed mental state is based on the monitoring of the biometric data by monitoring the user's heart rate using a heart rate sensor, and by monitoring the social media content by performing a contextual analysis of the social media content to determine the topic of the social media content and a sentiment of the user while engaging in communicating on social media regarding the topic of the social media content,
wherein the sentiment of the user is determined by using at least one selected from a group consisting of: facial analysis using a camera; and tonal analysis using a microphone, and
wherein the determining that the user has experienced a changed mental state comprises:
correlating the social media content and the biometric data; and
determining that the biometric data deviates from a normal range of the heart rate concurrently with the determined topic of the social media content matching a predefined topic and the determined sentiment matching a predefined sentiment, further comprising:

program instructions to select a caregiver from among a plurality of caregivers based on a biometric feedback loop analysis using the biometric data for the determined topic and an evaluation of past effectiveness of each of the caregivers in providing a positive impact on the user's sentiments in the past with regard to the determined topic, wherein the positive impact is determined by improvements in the user's biometric data and in determined sentiments of the user for the determined topic of the social media content; and program instructions to send a notification to a computer device of the selected caregiver of the changed mental state.

15. The method of claim 1, further comprising:

measuring an effectiveness of the selected caregiver based on the caregiver providing support to the user;

updating an effectiveness score of the selected caregiver based on the measuring;

determining, by the computer device and based on the measuring, that additional support is needed; and notifying, by the computer device, another caregiver of the changed mental state, wherein the monitoring of the biometric data includes monitoring of the user's pupil dilation using a smart contact lens on an eye of the user having an inward facing camera to observe the pupil dilation of the user, wherein the selecting the selected caregiver is based on user-defined associations, the changed mental state, an amount of deviation of the biometric from a normal range of the user, a determined topic of the social media content, and an effectiveness of each of the plurality of predefined caregivers.

* * * * *